(12) United States Patent
Henderson et al.

(10) Patent No.: US 6,716,578 B1
(45) Date of Patent: Apr. 6, 2004

(54) METHOD FOR SOLID STATE GENOME ANALYSIS

(75) Inventors: Eric Henderson, Ames, IA (US); Michael P. Lynch, Ames, IA (US)

(73) Assignee: BioForce Nanosciences, Inc., Ames, IA (US)

( * ) Notice: Subject to any disclaimer, the term of this patent is extended or adjusted under 35 U.S.C. 154(b) by 0 days.

(21) Appl. No.: 09/519,271

(22) Filed: Mar. 7, 2000

Related U.S. Application Data

(60) Provisional application No. 60/123,362, filed on Mar. 8, 1999.

(51) Int. Cl.⁷ .................. C12Q 1/68; G01N 1/30; G01N 33/543; G02B 21/00; G02B 21/26
(52) U.S. Cl. .................. 435/6; 435/40.5; 436/518; 436/524; 359/368; 359/391; 359/393; 359/394
(58) Field of Search .................. 435/6, 40.5; 436/518, 436/524; 359/368, 391, 393, 394

(56) References Cited

U.S. PATENT DOCUMENTS

| | | | |
|---|---|---|---|
| 5,143,854 A | 9/1992 | Pirrung et al. | 436/518 |
| 5,314,829 A | * 5/1994 | Coles | 436/165 |
| 5,445,971 A | * 8/1995 | Rohr | 436/526 |
| 5,514,540 A | 5/1996 | Teoule et al. | 435/5 |
| 5,514,550 A | 5/1996 | Findlay et al. | 435/6 |
| 5,670,322 A | 9/1997 | Eggers et al. | 435/6 |
| 5,760,300 A | * 6/1998 | Kajimura | 73/73 |
| 5,874,219 A | 2/1999 | Rava et al. | 435/6 |
| 5,965,133 A | 10/1999 | Cantor et al. | 424/179.1 |
| 5,981,733 A | 11/1999 | Gamble et al. | 536/25.3 |

FOREIGN PATENT DOCUMENTS

| | | |
|---|---|---|
| WO | WO9631775 | 10/1996 |

OTHER PUBLICATIONS

Pfannschmidt et al Nucleic Acids Research 1996. vol. 24, No. 9 pp. 1702–1709.*

Binning et al., *Surface studies by scanning tunneling microscopy* Phys. Rev. Lett., 1982, 49: pp. 57–61.

Cheng et al. *Electric field controlled preparation and hybridization analysis of DNA/RNA from E. coli on microlabricated bioelectronic chips*. Nature Biotechnology, 1998. 16: pp. 541–546.

Dammer et al., *Binding strength between cell adhesion protroglycans measured by atomic force microscopy*, Science, 1995, 267: pp. 1173–1175.

Dammer et al., *Specific antigen/antibody interactions measured by force microscopy*, Biophys. J., 1996. 70: pp. 2437–2441.

Florin et al., *Adhesion forces between individual ligan–receptor pairs*, Science, 1994, 264: pp. 415–417.

Fodor et al., *Light–directed spatially addressable parallel chemical synthesis*, Science, 1991, 251: pp. 767–773.

Fodor et al., *Multiplexed biochemical assays with biological chips*, Nature, 1993, 364: pp. 555–557.

Hinterdorfer et al., *Detection and localization of individual antibody–antigen recognition events by atomic force microscopy*, Proc. Natl. Acad. Sci., 1996 93: pp. 3477–3481.

Jones et al. *Microminiaturized immunoassays using atomic force imcroscopy and compositionally patterned antigen arrays*. Analy. Chem., 1998, 70(7): pp. 1233–1241.

Lee et al., *Direct measurement of the forces between complementary strands of DNA*, Science, 1994, 266: pp. 771–773.

Iyer et al., *The Transcription Program in the Response of Human Fibroblasts to Serum*, Science, 1999, 283(5398): pp. 83–87.

Moy et al., *Intermolecular Forces and Energies Between Ligands and Receptors*, Science, 1994, 266: pp. 415–417.

Rief et al, *Single Molecular Force Spectroscopy on Polysaccharodes by Atomic Force Microscopy*, Science, 1997, 275 pp. 1295–1297.

Rief et al, *Reversible Unfolding of Individual Titun Ig–domains by AFM* , Science 1997, 276: pp. 1109–1111.

* cited by examiner

*Primary Examiner*—John Brusca
*Assistant Examiner*—Shubo Zhou
(74) *Attorney, Agent, or Firm*—Michael Best & Friedrich LLP; Teresa J. Welch

(57) ABSTRACT

The invention is a solid state process for analyzing genomes by visualizing sequence specific markers (e.g., proteins that bind a defined DNA sequence elements) by scanning probe microscopy. The method includes linear display of the nucleic acid on a solid surface, image acquisition by the scanning probe microscope, and digital data analysis. The acts of the method result in a bar code type display of each fragment of the DNA sample. These bar codes are then used to place the fragments in the order they appear on the original DNA sample.

9 Claims, 1 Drawing Sheet

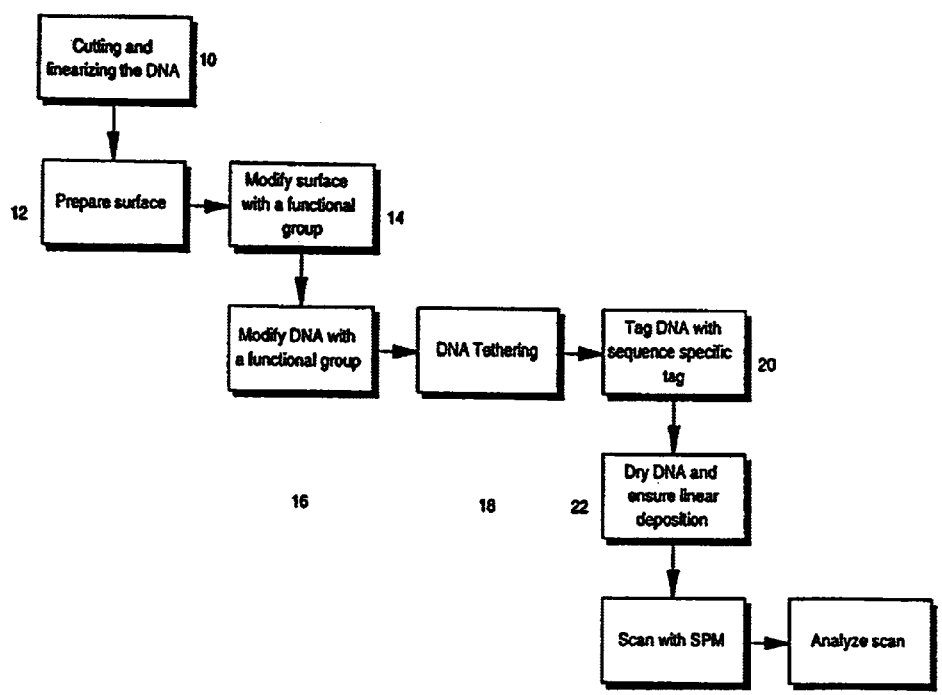

METHOD FOR SOLID STATE GENOME ANALYSIS

TECHNICAL FIELD

This application claims benefit from prior Provisional Application Ser. No. 60/123,362, filed Mar. 8, 1990.

This invention relates to the sequencing of DNA. More specifically, this invention is a method of mapping the relative positions of specific of nucleic acid using scanning probe microscopy.

BACKGROUND

The human genome project is arguably the largest and most important scientific collaboration in history. Of more importance is the fact that the human genomic project is just the beginning of the genome revolution. It is generally accepted that once the sequence of a genomic is known, it can be "mined" for information that will be invaluable in deriving useful products such as new drugs, genetic medicines, improved animal and plant produce, and a host of others. While current methods are adequate for the human genome project to reach is projected completion date early in this millennium, there is ample room for improvements in technologies that would facilitate genome mapping efforts.

While a small number of important genomes are under analysis or have been fully sequenced, current methods are costly and limited in their speed. The genomes of a wide variety of health related and agriculturally relevant organisms remain to be explored. Using current methodology to repeat the effort spent on the human genome for every animal and plant that remains to be studied would be laborious and extremely time consuming. It is therefore essential that technological improvements in current genome analysis methods be invented and implemented to aid in this undertaking.

Current Technology

The initial goal of all genomic projects is to acquire the highest quality sequence data for the genome being studied. This is accomplished by determining the nucleotide sequence of fragments of the genome, and then assembling these sequence fragments into the complete genome sequence. There are no methods in existence for direct sequencing of an entire genome greater than a few thousand base pairs in a single experiment.

The current method for sequencing genome involves first digesting the gemones with a restriction endonuclease. The genome is then subcloned into a variety of vectors including, but not limited to, plasmids, phage vectors, bacterial artificial chromosomes (BACs), and yeast artificial chromosomes (YACs). These fragments are still too large for direct sequencing, and must be further fragmented. The process of re-assembly of all the sequence information represented in these fragments is a formidable task. Current methods of genome analysis split the DNA (deoxyribonucleic acid) into many sub-genomic DNA fragments. These fragments are assembled into contiguous arrays known as "contigs." There are two general prior art approaches to forming these contigs.

One prior art method used to form contigs is to identify nucleotide sequences by creating "restriction maps" of DNA fragments. These DNA fragments can server to identify genomic fragments and also to identify the overlaps between fragments. A restriction map is a DNA profile that demarcates the positions of target sites for sequence specific restriction endonucleases along the length of the DNA. These maps are generated by digestion of the DNA with a restriction endonuclease and display of the digestion products by electrophoretic separation on a gel matrix, usually agarose or polyacrylamide. One advantage to this process is that it clearly defines which members of a large population or "library" of gene fragments still need to be sequenced, thereby eliminating undesirable redundancy of effort. Furthermore, once each fragment has been mapped, the maps themselves can be used to determine the order of the fragments in the original sample. This process facilitates their sequential assembly into contigs. This process provides fragment size information, but must be repeated several times with a number of variations to allow deduction of the restriction fragment order in large DNA sample. A need exists for a method that will reduce the effort, time and expense of the above method of nucleotide sequence mapping.

Other methods for characterizing genomic fragments also exist. For example, one common method known in the art as PCR footprinting uses defined sets of short oligonucleotide primers and generates a diagnostic set of PCR fragments from each genomic piece.

The second general prior art approach to genome analysis is to "shotgun" sequence randomly selected fragments and attempt to assemble them into the continuous genome sequence by locating sequence overlaps. This requires a large degree of redundancy in the sequencing effort. It is necessary to sequence many-fold more DNA than is contained in a single genome to insure that as many of the genes as possible have been included in the effort. While this approach works for small genomes, the requirement for redundancy of effort, coupled with the extremely low probability of obtaining sequence information for every gene in a genomic library, limit its utility. A need exists for a method that reduces the effort necessary to create these genomic libraries.

Both of these methods are facilitated by the use of physical markers to help identify the specific nucleotide sequence and produce a genomic map. The physical markers used can be produced in a variety of ways and with a wide range in precision. The markers can be genetic loci deduced from classical genetic approaches (e.g., genetic crosses and relative proximity analysis) or more direct methods such as fluorescence in situ hybridization analysis (FISH). The former process is laborious and can be time consuming, especially in the case of slow growing organisms or organisms for which the genetic manipulation tools are rudimentary at best. The latter process requires that prior knowledge about the sequence of the genes under scrutiny be available.

It must be noted that for mapping a genome, it is necessary to have two libraries, each constructed using a different restriction endonuclease. This way, the fragments in the two libraries will overlap (since the two different restriction endonucleases cut the genome at different locations). Thus, by mapping the two libraries, and comparing the results, regions of overlap are discovered and this determines the physical order of the fragments in the genome. These fragments can then be sequenced and the entire genomic sequence determined.

Gene Fragment Polymorphisms (GFPs)

In many cases it is of interest to compare DNA sequences from two sources. For example, in DNA "fingerprinting" applications one can use small variations in the sequence of DNA to determine the probability that a particular piece of DNA is derived from a given source. One method to do this is to compare the positions of target sites for endonucleases that cut DNA in a site specific fashion using a restriction endonuclease. If small changes have occurred in the defined DNA sequence from two sources, it is likely that the restriction endonuclease site map will reflect this, either by the gain or the loss of one or more sites. These changes are referred to as restriction fragment length polymorphisms, or RFLPs. RFLPs are a subset of all types of gene fragment polymorphisms, or GFPs, RFLP analysis is usually carried out by the conventional method described above, a restriction endonuclease digestion, followed by gel electrophoresis and Southern blotting. A need exists for a method of analyzing these GFPs that would reduce the time and labor involved, as well as the expenditure on reagents required by these steps.

Functional Sequence Mapping

A large portion of genomic DNA does not encode active genes. In addition, a significant portion of the functional component of a gene is never transcribed into RNA or used to construct a protein. However, these regulatory regions of genes are critical for expression of the gene product and play key roles as, for example, targets for new drugs that regulate levels of gene expression. To discover which regions are functional and which are not, with regard to gene activity, it is often necessary to do a large number of studies with large populations of sub fragments of the genome. This practice can take years of redundant, laborious, and expensive work.

Scanning Probe Microscopy and Atomic Force Microscopy

A scanning probe microscope (SPM) utilizes a probe which is scanned over a surface. The interaction between the probe and surface is detected, recorded, and displayed. If the probe is small and kept very close to the surface, the resolution of the SPM can be very high, even on the atomic scale in some cases. There is a wide variety of SPM instruments capable of detecting optical, electronic, conductive, and other properties. One form of SPM, the atomic force microscope (AFM) is an ultra-sensitive force transduction system. In the AFM, a sharp tip is situated at the end of a flexible cantilever and scanned over a sample surface. While scanning, the cantilever is deflected by the net sum of the attractive and repulsive forces between the tip and sample. If the spring constant of the cantilever is known, the net interaction force can be accurately determined from the deflection of the cantilever. The deflection of the cantilever is usually measured by the reflection of a focused laser beam from the back of the cantilever onto a split photodiode, constituting an "optical lever" or "beam deflection" mechanism. Other methods for the detection of cantilever deflection include interferometry and piezoelectric strain gauges. The first AFMs recorded only the vertical displacements of the cantilever. More recent methods involve resonating the tip and allowing only transient contact, or in some cases no contact at all, between it and the sample. Plots of tip displacement or resonance changes as it traverses a sample surface are used to generate topographic images. Such images have revealed the 3D structure of a wide variety of sample types including material, chemical and biological specimens. Some examples of the latter include DNA, proteins, chromatin, chromosomes, ion channels, and even living cells.

In addition to its imaging capabilities, the AFM can directly sense and measure forces in the microNewton (10') to picoNewton (10') range. Thus, the AFM can measure forces between molecular pairs, and even within single molecules. Moreover, the AFM can measure a wide variety of other forces and phenomena, such as magnetic fields, thermal gradients and viscoelasticity. This ability can be exploited to map force fields on a sample surface, and reveal with light resolution the location and magnitude of the these fields, as in, for example, localizing magnetic microparticles tethered to biomolecular complexes of interest.

BRIEF DESCRIPTION OF THE DRAWINGS

FIG. 1 is a block diagram of the acts that comprise the method of the present invention.

SUMMARY

One embodiment of the present invention relates to a method for determining the order of nucleic acid segments from a nucleic acid sample, the method comprising tagging sequence-specific sites of the nucleic acid sample with a sequence specific tag, scanning the nucleic acid sample using a scanning probe microscope, and analyzing the scan of the nucleic acid sample to determine the order of nucleic acid segments.

A method for comparing DNA from two different sources, the method comprising tagging specific segments of a nucleic acid sample from a first source using a sequence specific tag, tagging specific segments of the nucleic acid sample from a second source using a sequence specific tag, scanning the tagged nucleic acid sample from the first source using a scanning probe microscope, scanning the tagged nucleic acid sample from the second source using a scanning probe microscope, analyzing the scan from the first source and the scan from the second source using a computer, and comparing the scan from the first source to the second source.

This embodiment analyzes DNA by way of example, but the present invention contemplates that any type of nucleic acid can be used as a sample in the sequencing method.

An object of this invention is use of SPM technology to identify defined sequence elements in nucleic acids fragments. The SPM scan further aids in the determination of the order of these elements on the nucleic acid of interest.

Another object of the present invention is to provide a method for simplifying DNA fingerprinting analysis.

A further object of the present invention is to provide a method for simplifying functional mapping of DNA fragments.

Yet another object of the present invention is a method for simplifying the mapping of DNA fragments such as BAC's and YAC's.

DETAILED DESCRIPTION

The embodiment of the present invention disclosed herein is a method for analysis of populations of genomes and genomic fragments using a scanning probe microscope, such as an atomic force microscope or near field optical microscope. The physical maps created by this approach constitute genetic "bar codes" that can be used in a wide variety of gene identification and characterization applications. This method can be used to help the re-assembly of mapped DNA fragments back into the correct order. The AFM may also be used for rapid and precise mapping of target DNA samples such as cosmids, bacterial artificial chromosomes (BACs) and yeast artificial chromosomes (YACs). The invention described here also allows study of RFLPs, length polymorphisms generated by PCR methods, and other forms of GFPs (e.g., single point mutations). The AFM is used here by way of example, but this does not exclude use of other types of SPM instrumentation.

FIG. 1 shows the acts that constitute the method of the present invention. In this embodiment a dipstick is used as the substrate onto which the functionalized DNA is bound for analysis. This dipstick facilitates the rapid mapping and analysis of sequence specific markers bound to large DNA molecules. However, the substrate to which the DNA is tethered is not exclusively in this form. The substrate for the tethering surface could be made of any compatible material known in the art and shaped in any form that can be scanned by the SPM instrumentation.

The DNA sample is first cut from the source and linearized (10). This material is then set aside while the dipstick surface is prepared (12). The dipstick surface is prepared by modifying it with a chemically reactive functional group so that the DNA can be tethered to the surface for eventual scanning by the SPM (14). The next step is modifying the DNA sample with the appropriate functional group (16). This step will facilitate binding the DNA to the dipstick surface later in the method. Once the DNA is functionally modified, the DNA is then tethered to the dipstick surface (18). After the DNA is properly tethered, it is tagged with a sequence specific tag (20). The sequence specific tag is what is read (i.e., measured or detected) by the SPM. The tagged DNA is then dried (22) and aligned in a linear fashion on the dipstick surface. Drying ensures more stable imaging conditions and, therefore, optimizes data acquisition, although a drying step is not absolutely required. The tagged and tethered DNA on the dipstick is now scanned using the SPM instrument (24). In the last step, the readout from the SPM is analyzed (26).

Many of the steps of the present invention are not necessarily specific to the order as laid out in the following present embodiment. This embodiment is given by way of example. For instance, the surface can be prepared and modified after the DNA is functionalized instead of before.

Cutting/Linearization

The first step of the method of the present invention involves obtaining the DNA sample to be analyzed (10). This is accomplished by cutting and linearizing the DNA to be analyzed. The DNA can be prepared by fragmenting the desired genomic DNA and ligating the fragments in a typical cloning vector known to those skilled in the art. The DNA can be excised from the source plasmid, cosmid, BAC, YAC or any nucleic acid vector using Bam III (*Bacillus amyloliquefaciens II*), EcoRI (*E. Coli* restriction endonuclease number 1), or any comparable restriction endonuclease, or other nuclease. DNA can also be prepared by mechanical methods such as shearing. The reaction conditions are determined by the choice of endonuclease and are common knowledge to those skilled in the art. The present embodiment utilizes a DNA sample from a bacterial virus or phage, termed Lambda. This DNA sample is 48.502 base pairs long and constitutes the entire genomic of the Lambda phage.

Surface Preparation

The next act of the method is the selection of a surface (12). This surface will be the site where the DNA is deposited. The embodiment of the present invention utilizes a dipstick substrate to which to bind the DNA sample for scanning. In the present embodiment the dipstick is made of Teflon. Other plastics or inert polymers can be used in alternative embodiments. A small pad made of mica is attached to one end of the Teflon dipstick. Other embodiments may incorporate pads made of polished silicon or some similar material that is sufficiently flat to allow resolution of DNA fragments by AFM. Other surfaces include episilicon, highly ordered pyrolytic graphic, sapphire, gypsum, or coating with polystyrene and other defined surface coating materials. Any of these surfaces can also can be coated with gold to facilitate formation of self assembled monolayers from alkanethiolate solutions. The advantage to this approach facilitates presentation of a wide variety of surface chemistries for various applications.

Surface Modification

Once the dipstick surface is prepared, then the surface must be modified (14) so that it will react and tether the DNA for analysis. In the present embodiment the ability of alkanethiolates to form robust monolayeres on gold surfaces is exploited. The gold is then coated with a chemically reactive alkanethiolate monolayer, the reactive portion in this example being either a carboxyl or succinimide group. These chemically active surfaces then serve as attachment points for the modified DNA.

In this embodiment a molecule containing a sulfhydral group at one end, an 11 carbon alkane chain, and a succinimide group at the other end is used. This molecule is dissolved in pure ethanol to a final concentration of 1 mM. The gold coated surface is incubated in this solution for several hours at room temperature, allowing a stable monolayer to form. DNA that contains an amino group modification at the terminus can then be immobilized on this surface by formation of an amide bond between the succinimide group on the alkane and the primary amine on the DNA.

An advantage of this method is that it can be used to create by hydrophilic domains surrounded by hydrophobic domains to which the DNA will not have a high affinity in solution. This facilitates "floating" the DNA away from the surface during the tagging procedure in minimize sterochemical hindrance, then deposition of the DNA and the surface by virtue of dehumidification, which abrogates the hydrophobic effect. To create these surfaces, the first step is to produce a uniform monolayer of methyl-terminated (hydrophobic) alkanethiolates on a gold surface. The gold surface can be modified with a pattern such as stripes or checkerboard arrays by evaporation of gold through a mask in order to create different areas to which to bind the DNA. UV light is then passed through a mask to oxidize the sulfur atom on the alkanethiolate. This treatment weakens the sulfur gold interaction considerably, but only in those regions subjected to the UV irradiation. Subsequent addition of a succinimide terminated alkanethiolate results in replacement of the oxidized thiolates with the succinimide terminated molecules and creation of a patterned array of chemically active domains to which DNA can be specifically tethered. Variations of this method are known to those skilled in the art.

Alternative methods for surface modification include preparing a positively charged surface by modification of the surface using a silane compound containing primary amines. Another embodiment includes spin coating a mica or polished silicon surface with a preparation of polystyrene. The polystyrene is prepared by dissolution in toluene. Each one of these alternative methods for surface modification will have a resulting alternative embodiment for the DNA modification of the next step. A functional group must be placed on the DNA that will correspondingly react with the surface to tether the DNA. The present invention contemplates utilizing any of these alternative methods.

DNA Modifications

Linearized DNA is modified at one or both ends with a reactive group that allows the DNA molecule to be firmly tethered to a surface (16). In this embodiment, the DNA is modified with a primary amine group to allow covalent bonding to the surface bound succinimide group. The linearized DNA contains staggered or "sticky" ends by virtue of its release from the cloning victor by a restriction endonuclease, or, in the case described above (Lambda DNA) the natural ends of the Lambda genomic are staggered (note the fragments cleaved from cosmids at the COS site will have the same 12 nucleotide sticky end as Lambda phage). Since this sequence is known, a complementary molecule containing the amino terminal group is synthesized by standard methods known to those skilled in the art. This material can alternatively by purchased from a commercial vendor of synthetic DNA oligonucleotides. The amino terminated oligonucleotide is ligated to the linearized DNA fragment using T4 DNA ligase and standard conditions known to those skilled in the art. The ligation product is then rapidly purified chromatographically and tethered to the surface as described below. Other methods known to those skilled in the art can likewise be used to separate large and small DNA fragments.

DNA Deposition and Tethering DNA to the Surface

Although the details of DNA deposition vary the present embodiment contemplates depositing a small droplet of DNA solution on a surface and allowing the DNA to bind to the surface through and end-specific tether (18).

In the present embodiment, the DNA is dissolved in a solution of 10 mM Phosphate buffer, Ph 8.0. Common buffers like Tris are not appropriate because they contain primary amines. Other primary amines besides the one on the DNA fragment can interfere with this step in the method. The DNA is then loaded into a piezo driven microjet device (similar to that used in an ink jet printer, but used for biological deposition and a microdroplet of the DNA solution is ejected and deposited on the succinimide surface. For large DNA fragments this process can be too vigorous and result in shearing of the DNA. In these cases the problem can be solved by depositing the DNA using a pin tool device. A pin tool is a mechanical device with a sharp point that picks up a small quantity of the DNA solution and deposits it at a desired location by direct contact and capillary transfer from the pin tool to the surface.

The DNA is allowed to covalently bind to the surface by maintaining the humidity above (60°, RH for an hour at room temperature. Unbound materials are washed away and the bound material is used for subsequent mapping. This one embodiment of the deposition procedure and is not meant to exclude other methods for deposition of end-tagged DNA molecules to specific locations on a surface.

While it is possible to map sequence-specific tags on DNA that is not tethered or localized on a surface, there are significant advantages to having the DNA tethered at one end in a defined location. This provides spatial coordinates to which different DNA molecular species are assigned. In this way, an array of DNA molecules is analyzed on a single surface without the introduction of any ambiguity regarding the identification of the DNA fragment under scrutiny. Each molecular species is located at a well defined spatial address in the array. When the DNA is tethered to a defined spatial address the AFM can be instructed to automatically access those addresses sequentially. These steps may significantly reduce search time.

Sequence Specific Tagging of Immobilized DNA

In the next step the DNA is tagged with a sequence specific tag (20). In the present embodiment the DNA is incubated with a mutated restriction endonuclease in a typical restriction endonuclease reaction solution (25 mM buffer, pH 7.6: 100 mM monovalent cation, typically Na, 10 mM divalent cation, typically $Mg^+$, 0.5 mM reducing agent, typically dithiothreitol). The mutant restriction endonuclease has been modified by amino acid substitution within its catalytic pocket such that the endonuclease can bind its DNA target site, but is incapable of cutting the DNA. This substitution promotes DNA binding but inhibits cleavage, (see D. Allison, P. Kerper, M. Doktyez, J. Spain, P. Modrich, F. Larimer, T. Thundat, and R. Warmack, Proc. Natl. Acad. Sci. USA, 1996, 93: p. 8826–8829). This is accomplished by genetic engineering methods known to practitioners skilled in the art.

Wild type restriction enzymes can also be used by substituting $Ca^+$ or $Mn^+$ for $Mg^+$, the common catalytic divalent cation. In the presence of $Ca^+$ or $Mn^+$, but the absence of $Mg^+$, many restriction endonucleases will bind out not cleave DNA. This is because $Mg^+$ is required for catalytic activity of the endonuclease. The conditions for binding but not cutting of the DNA for each restriction endonuclease used are optimized using electrophoretic mobility shift experiments, a method whose application for this purpose is common knowledge to those skilled in the art.

The restriction endonuclease tag binds to the DNA, and the surface is quickly rinsed to remove spuriously bound tag molecules and other debris, such as excess salt. In some cases the tag can be fixed in position using UV light or a crosslinker such as gluteraldehyde. Other endonucleases can be used that have been modified such that they bind tightly to DNA but do not cut the DNA molecule. Those endonucleases that bind tightly to a defined nucleotide sequence, but do not cut the DNA target, are suitable for gene mapping experiments. Other types of materials that can be used for tagging specific sequences of the nucleic acid include transcription factors, nucleotides, modified nucleotides, peptides, functional protein markers, or a duplex, triplex or quadruplex forming nucleic acid molecule, or a small molecule conjugated to a microparticle or a nanoparticle.

The description of the present embodiment tag does not exclude the use of other tags that might be incorporated into the method of the present invention. The DNA is generally tethered prior to tagging with site specific markers. However, the sequence of events can be altered such that the DNA is first tagged, then tethered by the methods described herein for analysis by AFM.

Drying and Depositing in a Linear Fashion

Next, the tethered and tagged DNA sample must be dried and laid out on the dipstick in a linear manner (22). In the present embodiment a stream of low moisture inert gas is used. A stream of gas, such as argon, is bled from a source, such as a canister, over the dipstick. This dry inert gas carriers away any leftover moisture from the tagging step. Furthermore, as this dry inert gas is held over the dipstick the inert gas leaves the nucleic acid sample oriented in a uniform direction. Having the nucleic acid samples dried in a flat and uniform direction aids in the scanning step of the process.

Alternatively, drying and linear deposition of the samples (22) can be done by several other techniques known in the art. For examples a number of methods include unidirectional fluid flow (for linear display) and electromotive force (for linear display). In addition, previous reports have shown that DNA can be aligned on a surface by slow retraction of a meniscus as the DNA is dried. (For an explanation, see Bensimon, A., A. Simon, A. Chiffaudel, V. Croquette, F. Heslot, and D. Bensimon, Science, 1994, 265: p. 2096–2098.)

Scanning

Scanning of the tagged nucleic acid sample in the present embodiment is done utilizing an atomic force microscope (24). The sample is placed in the instrument. A Digital Instruments, Inc., Dimension 3100 is used in this embodiment and is controlled by a computer and software generally available. The computer controls the operation of the tip across the dipstick. In the present embodiment the nucleic acid samples have been tethered to specific sites on the stick. The computer can automatically scan these sections and report where the tags are found, and measure both the contour locations of the tags as well as the distance between the contours. Knowing where the DNA is specifically bound to the surface aids the analysis of the scan. Since the conventional AFM is limited in scan field size to about 100 square microns, knowing where the DNA array is located and the positions of the DNA molecules within the array greatly speeds the scanning process. Therefore, each array of DNA molecules is initially located through the use of a physical mark such as an indentation or ink spot, then the array is scanned and the positions of the molecules within the array noted.

The analysis conditions of this embodiment require low humidity because it minimizes potentially destructive tip-sample capillary forces and provides a more stable DNA specimen. The instrument takes data scans of the different sequence specific tags it has located and then feeds this data to the user who can analyze the output. In other embodiments low humidity might not be desirable, i.e. using the above method and scanning the sample while in solution.

Because in the present embodiment the DNA is displayed in an ordered array on solid state surfaces, the array can be processed continuously in the SPM. Through the use of indexing markers on the surface of the dipstick, the instrumentation can know precisely the position of the current scan, and therefore the sample that is currently being processed. A bar code is assigned to the known sample, making that DNA fragment uniquely identifiable thereafter by virtue of its bar code.

Analyzing the Scan

Software known by those skilled in the art runs the scan by the AFM (26). This software utilizes pattern recognition algorithms that direct the instrumentation to produce a hardcopy output.

In the present embodiment, the AFM data is collected using commercial software supplied with the instrument. This data is then ported to a separate computer using a software program called IDEAS (NanoStar, Balitmore, Md.). IDEAS searches the field and finds continuous data profiles that correspond to intact, linear DNA molecules. IDEAS then measures the contour length of the molecules and locates the physical markers comprised of bound EcoRI molecules. The software then plots these locations as a function of fragment length and generates a histogram showing the probability of finding a physical marker at a given position along the length of the DNA molecule. These data are averaged and used to generate a diagnostic bar code for that particular DNA molecule. By measuring the distance between the tags, the length of the DNA fragment between the tags can be ascertained. The order in which the segments appear on the contig, can be learned utilizing data from several different tagged nucleic acid samples.

The bar codes represent the nucleic acid fragment. Each bar of the code is where the AFM has found one of the sequence specific tags. The distances between the bars is the distance between the located tags. By aligning the bars from separate bar codes, the order of each known fragment can be determined.

The scan can be analyzed by several other methods known in the art. The most basic method of analyzing the scan is to measure by hand the contours that have been given as output from the SPM instrument.

The alternative embodiments could utilize a computer program which could analyze the information on the location of the sequence specific tags and the distance between them. This computer then would use an algorithm to place the fragments in the proper order as they appear on the original nucleic acid sample.

An advantage to the present invention is the bar code system of analyzing the scans. Utilizing a bar code enables faster ordering of the fragments. Before, researchers had to map the sequence of the fragment in order to determine the order of the fragments in the sample. The present invention allows the user to utilize the bar code of each fragment to align the overlapping fragments in the order they appear on the cosmid without having to determine the sequence of large sections of the sample.

Further Embodiments and Advantages

An alternative embodiment could be to apply this method to comparing DNA sequences from two sources. To do this, a sequence specific tag would be utilized that would bind onto an area where it is thought a nucleotide sequence variation might occur. Once the sequence specific tags were placed on the DNA fragments utilizing the method described above, the fragments would be scanned in the SPM. If a tag appears on a section of the DNA in both the samples then it would increase the likelihood that the samples came from the same source. By choosing the sequence specific tag that binds on to an unusual nucleotide sequence, accurate fingerprinting can be done without the long process of restriction fragment length polymorphisms utilizing gel electrophoresis and Southern blotting.

A further embodiment of the present invention involves functional sequence mapping. As discussed above, a large portion of genomic DNA does not encode active genes. Using the above method this invention allows a rapid analysis of genomes using markers that specifically tag regions involved in gene activity. Once the DNA is tagged with these sequence specific markers, the DNA fragment can by analyzed by the SPM. The location of the sequence specific tags will report where the active encoding regions are located on the original DNA fragment.

A further embodiment of the present invention involves identification of single nucleotide polymorphisms. It has been suggested that individual humans have a single nucleotide variation relative to any other individual every 900 basepairs. These variations can be valuable markers associated with genetic traits such as predisposition to disease. The maps generated by the method described here can reveal single nucleotide polymorphisms because such a change in sequence can preclude or allow binding of the tag to a particular sequence element.

The information and examples described herein are for illustrative purposes and are not meant to exclude any derivations or alternative methods that are within the conceptual context of the invention. It is contemplated that various deviations can be made to this embodiment without deviating from the scope of the present invention. Accordingly, it is intended that the scope of the present invention be dictated by the appended claims rather than by the foregoing description of this embodiment.

We claim:

1. A method for analyzing a nucleic acid sample comprising:
    (a) obtaining a nucleic acid sample by cutting and linearizing a stand of nucleic acid;
    (b) preparing a surface;
    (c) tethering the linearized nucleic acid sample to the surface;
    (d) tagging two or more sequence specific sites of the tethered nucleic acid sample with a sequence specific tag,
    (e) drying the nucleic acid sample;
    (f) scanning the nucleic acid sample with a scanning probe microscope; and (g) analyzing the scan to determine the distance between the tagged nucleic acid sites.

2. The method of claim 1, wherein preparing the surface further comprises modifying the surface with an alkanethiolate.

3. The method of claim 1, wherein tethering the linearized nucleic acid sample to the surface further comprises modifying one or both ends of the nucleic acid sample with a reactive group that will react with the prepared surface.

4. The method of claim 1, wherein scanning the nucleic acid sample further comprises bleeding a low moisture inert gas over the tethered nucleic acid sample.

5. The method of claim 1, wherein analyzing the scan further comprises forming bar code readouts wherein the bars represent a tagged nucleic acid sample and the distance between the bars represents the distance between the tagged sequence specific sites.

6. The method of claim 1, further comprising tethering the nucleic acid sample to a deposition surface.

7. The method of claim 6, wherein the deposition surface is on a dipstick.

8. The method of claim 7, wherein the deposition surface on the dipstick has specific areas for tethering different types of the nucleic acid sequences.

9. The method for analyzing a nucleic acid sample comprising:
(a) obtaining a nucleic acid sample by cutting and linearizing a strand of nucleic acid;
(b) preparing a surface,
(c) tethering the linearized nucleic acid sample to the surface;
(d) tagging two or more sequence specific sites of the tethered nucleic acid sample with a sequence specific tag,
(e) scanning the nucleic acid sample with a scanning probe microscope; and
(f) analyzing the scan to determine the distance between the tagged nucleic acid sites.

* * * * *